(12) United States Patent
Sirinyan et al.

(10) Patent No.: US 7,025,978 B1
(45) Date of Patent: Apr. 11, 2006

(54) USE OF POLYSILOXANES CONTAINING QUARTERNARY AMINO GROUPS AS FORMULATION AUXILIARY AGENTS, AND AGENTS CONTAINING THE SAME

(75) Inventors: Kirkor Sirinyan, Bergisch Gladbach (DE); Kerstin Heinen, Bergisch Gladbach (DE)

(73) Assignee: Bayer AG, Leverkusen (DE)

( * ) Notice: Subject to any disclaimer, the term of this patent is extended or adjusted under 35 U.S.C. 154(b) by 136 days.

(21) Appl. No.: 10/129,774

(22) PCT Filed: Oct. 31, 2000

(86) PCT No.: PCT/EP00/10767

§ 371 (c)(1),
(2), (4) Date: May 9, 2002

(87) PCT Pub. No.: WO01/35739

PCT Pub. Date: May 25, 2001

(30) Foreign Application Priority Data

Nov. 12, 1999 (DE) .......................... 199 54 394

(51) Int. Cl.
*A01N 25/32* (2006.01)

(52) U.S. Cl. ........................ 424/406; 424/405; 424/411; 514/386; 514/531

(58) Field of Classification Search .............. 424/405, 424/406, 451, 455, 411; 514/386, 531
See application file for complete search history.

(56) References Cited

U.S. PATENT DOCUMENTS

| 4,342,742 | A | 8/1982 | Sebag et al. .................. 424/59 |
| 4,609,750 | A | 9/1986 | Kollmeier et al. .......... 556/419 |
| 4,654,161 | A | 3/1987 | Kollmeier et al. ...... 252/174.15 |
| 4,833,225 | A | 5/1989 | Schaefer et al. ............... 528/28 |
| 4,874,753 | A | 10/1989 | Baker .......................... 514/89 |
| 4,891,166 | A | 1/1990 | Schaefer et al. .......... 260/404.5 |
| 5,130,135 | A | 7/1992 | Van Tonder ................. 424/405 |
| 5,236,954 | A | 8/1993 | Gladney et al. ............. 514/531 |
| 5,466,458 | A | 11/1995 | Martin et al. ................ 424/405 |
| 5,846,997 | A | 12/1998 | Sirinyan et al. ............. 514/490 |

FOREIGN PATENT DOCUMENTS

| AU | 627 847 | 9/1992 |
| DE | 44 43 062 | 6/1996 |
| DE | 19519007 | * 11/1996 |
| DE | 198 07 630 | 8/1999 |
| EP | 0 017 121 | 4/1983 |
| EP | 0 017 122 | 6/1983 |
| EP | 0 436 359 | 7/1991 |
| EP | 0 137 627 | 1/1992 |
| EP | 0 484 857 | 5/1992 |
| EP | 0 710 688 | 5/1996 |
| GB | 2135886 | 9/1984 |

OTHER PUBLICATIONS

Bio Spot—Label, 1998.*

* cited by examiner

*Primary Examiner*—Neil S. Levy

(57) ABSTRACT

The present invention relates to the use of polysiloxanes containing at least one quaternary ammonium group as formulation auxiliaries in formulations of pharmaceutically and veterinary active compounds, and to compositions comprising
a) pharmaceutically or veterinary active compound and
b) a polysiloxane derivative containing at least one quaternary ammonium group per molecule,
if appropriate, further auxiliaries and carriers.

3 Claims, No Drawings

USE OF POLYSILOXANES CONTAINING QUARTERNARY AMINO GROUPS AS FORMULATION AUXILIARY AGENTS, AND AGENTS CONTAINING THE SAME

A large number of polysiloxanes having terminal quaternary amino groups and their use as so-called "Conditioners" in shampoos and hair-care compositions are known from EP-A 0 017 121, 0 017 122, 0 282 720, 0 294 642, 0 166 122 and 0 164 668.

A problem which is frequently encountered in the preparation of active compound formulations in the field of pharmacy and veterinary medicine is, in particular in the case of aqueous formulations, the insufficient solubility of the active compounds, and the associated insufficient storage-stability of the finished formulations.

To use active compounds, some of which are difficult to dissolve in water, in the form of dermally applicable liquid formulations, it is necessary to prepare homogeneous solutions or emulsions based on organic solvents and insecticidally active compounds. To this end, the active compounds are usually dissolved in organic solvents, such as isopropanol, 2-butoxyethyl acetate, ethylene glycol diacetate, and, if appropriate, mixed with further additives. The preparation of such formulations is described in U.S. Pat. No. 4,874,753, EP-A 137 627 and GB 2 135 886. Said systems have the disadvantages that, for example when active compounds from the class of the pyrethrins and pyrethroids, in particular α-cyanopyrethroids are used, they lead to severe skin irritations and furthermore have a short long-term action. It is desirable to replace these formulations by formulations which are skin-compatible and toxicologically acceptable and have a long-term action of several weeks.

To remedy said disadvantage, for example of the known pyrethroids and pyrethrins, patents AU-627 847, EP-A 413 610 propose to dissolve these active compounds in high-boiling solvents, such as monopropylene glycol, which additionally contain natural skin-compatible oils, such as pine oil, sunflower oil or soya oil. Furthermore, patent WO 91/13545 discloses that highly effective skin-compatible liquid formulations can be prepared by dissolving said active compounds in amounts of >50% in aliphatic solvents, such as 2-(2-butoxyethoxy)ethanol or 2-(2methoxyethoxy) ethanol. These formulations have the disadvantage that they require the use of relatively large amounts of active compounds and, furthermore, lead to skin irritations in sensitive animal varieties. To achieve an acceptable biological effect with the use of low amounts of active compound, U.S. Pat. No. 5,466,458 proposes the use of emulsions based on said active compounds with long-chain aliphatic amines or alcohols, such as hexadecan-1-ol, 1-octadecylamine. The use of the long-chain amines has the disadvantage that, over the course of time, they degrade said active compounds. In most cases, formulations based on long-chain alcohols have insufficient long-term action.

Surprisingly, these objects are achieved by the use according to the invention of the abovementioned polysiloxanes. Clear solutions or emulsions of high storage stability are formed.

Furthermore, the use according to the invention of these polysiloxanes surprisingly leads to improved compatibility and an activity-enhancing synergistic effect, in particular in combination with pyrethroids and pyrethrins.

Accordingly, the present invention relates to the use of polysiloxanes containing at least one quaternary ammonium group as formulation auxiliaries in formulations of pharmaceutically and veterinary active compounds.

The present application further provides novel compositions, comprising
a) at least one pharmaceutically or veterinary active compound and
b) a polysiloxane derivative containing at least one quaternary ammonium group per molecule,
if appropriate, further auxiliaries and carriers.

The compositions according to the invention are, in particular, highly suitable for preparing aerosol sprays, pump sprays, spot-on formulations and pour-On formulations for use in the control of parasites on animals.

To prepare the compositions according to the invention, it is possible to use, in general, all active compounds from the pharmaceutical and veterinary field.

By way of example, but not by way of limitation, the active compounds which are also mentioned as suitable combination partners in this publication (see below) may be mentioned (for example chloronicotinyl compounds and pyrazoles).

Particularly suitable active compounds are the pyrethrins and pyrethroids with common names such as fenvalerate [α-cyano-3-phenoxybenzyl α-(p-Clphenyl)-isovalerate], flumethrin [(α-cyano-4-fluoro-3-phenoxy)benzyl 3-[2-(4-chlorophenyl)-2-chlorovinyl]-2,2-dimethylcyclopropane carboxylate] and its enantiomers and stereoisomers, cyfluthrin [(α-cyano-4-fluoro-3-phenoxy)benzyl 2,2dimethyl-3-(2,2-(2,2-dichlorovinyl) cyclopropanecarboxylate, permethrin [3-phenoxybenzyl cis, trans-3-(2,2-dichlorovinyl)-2,2-dimethylcyclopropanecarboxylate], cypermethrin [α-cyano-3-phenoxybenzyl 2,2-dimethyl3-(2,2-dichlorovinyl) cyclopropanecarboxylate, deltamethrin [α-cyano-3-phenoxybenzyl cis, trans-3-(2,2-dibromovinyl)-2,2-dimethylcyclopropanecarboxylate], fluvalinate [2-cyano-3-phenoxybenzyl 2-(2-chloro-α,α,α-trifluoro-p-toluido)3-methylbutyrate, where pyrethroids having acaricidal action are preferred for preparing the novel formulations and those based on α-cyanopyrethroids, such as esters of the α-cyano-3-phenylbenzyl alcohols or 4-fluoro-α-cyano-3-phenoxybenzyl alcohols are particularly preferred. Very particular preference is given to flumethrin.

The amounts of active compound can be varied within wide limits, between 0.1 and 15%. Amounts in the range of 0.1–7.5% are preferred. Particular preference for preparing the novel formulations according to the invention is given to using amounts in the range from 0.2–2.0%. Here, percentages are based on percent by weight.

It is, of course, also possible to use further active compounds as combination partners in the compositions according to the invention.

Combination compounds which may be mentioned as being preferred are the insecticides used in the control of ectoparasitic insects, such as nicotinyl and, in particular, chloronicotinyl insecticides, N-phenylpyrazoles, carbamates, phosphoric and phosphonic esters, growth inhibitors or mixtures of these active compounds with one another, and their mixtures with synergists. In the context of this application, synergists are understood as meaning compounds which do not on their own have the desired activity but which, as mixing partners, lead to an increase of the activity of the a.i.

Chloronicotinyl insecticides which may be mentioned are compounds of the Formulae (I), (II) and (III):

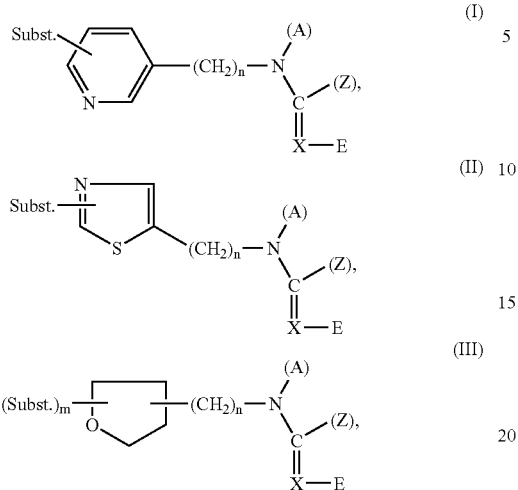

in which
n represents 1 or 2,
m represents, 0, 1 or 2,
Subst. represents one of the substituents listed above, in particular halogen, very particularly chlorine,
A, Z, X and E are as defined above.
In particular, the following compounds may be mentioned:

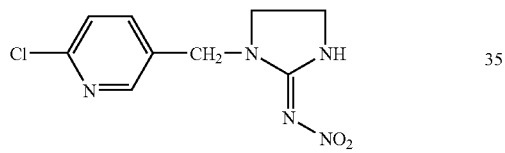
imidacloprid

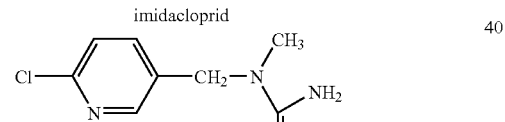

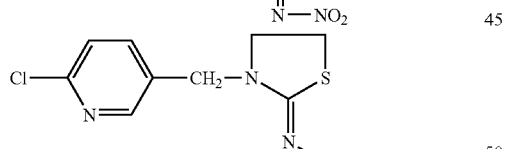

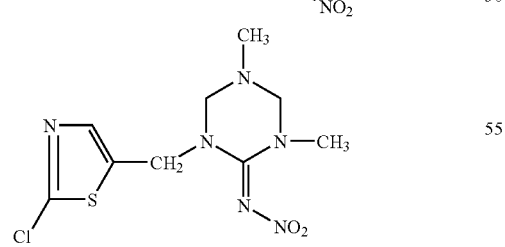
AKD 1022

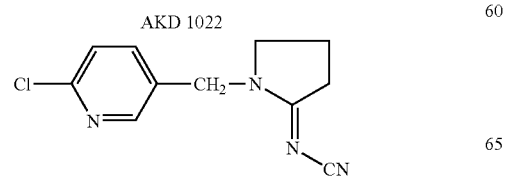

-continued

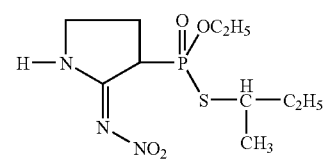

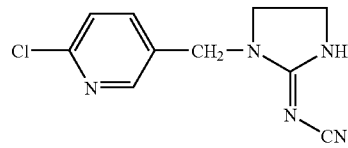

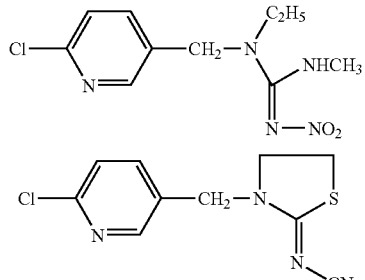

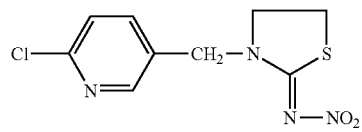
thiacloprid

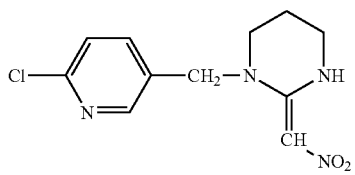

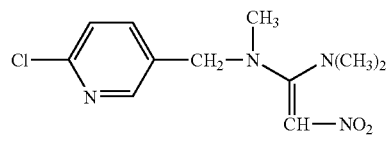

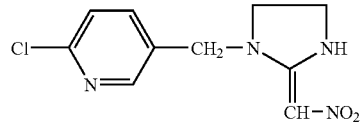

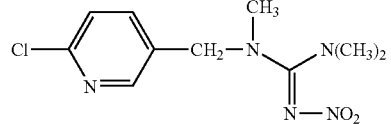

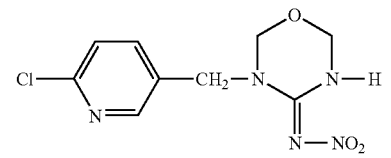

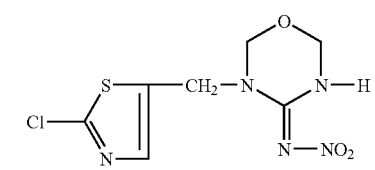

-continued
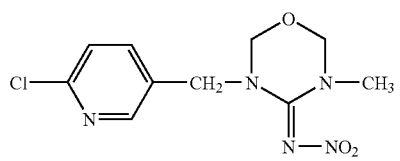
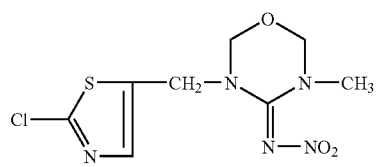
thiamethoxam
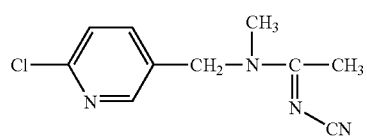
acetamiprid
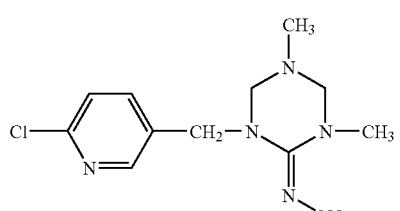
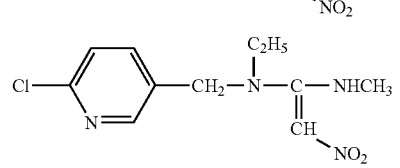
nitenpyram
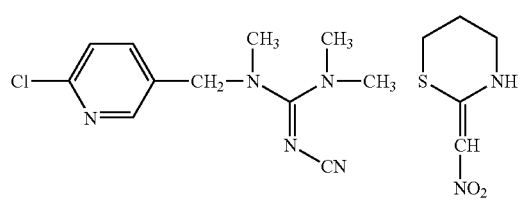
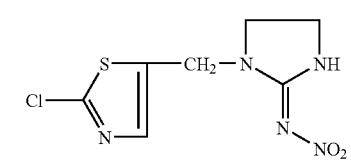
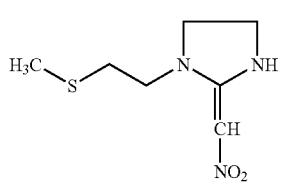
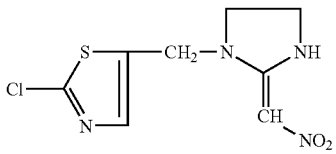
-continued
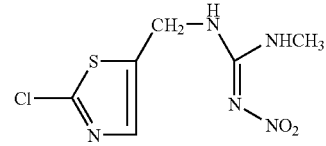
chlothianidine
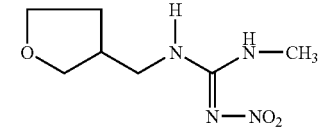
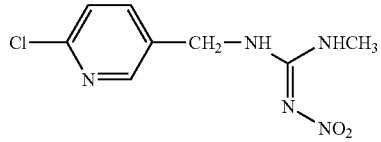
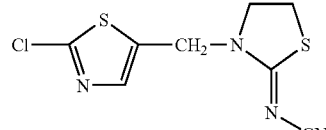
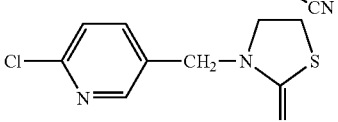
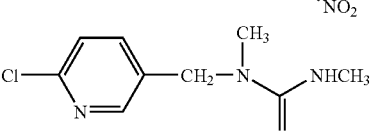
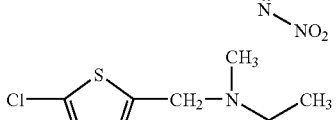
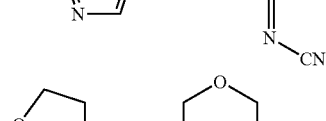
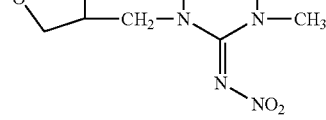
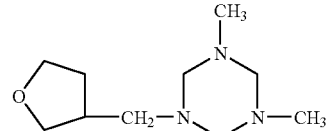
Particular emphasis is given to the compounds
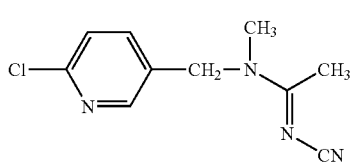

-continued

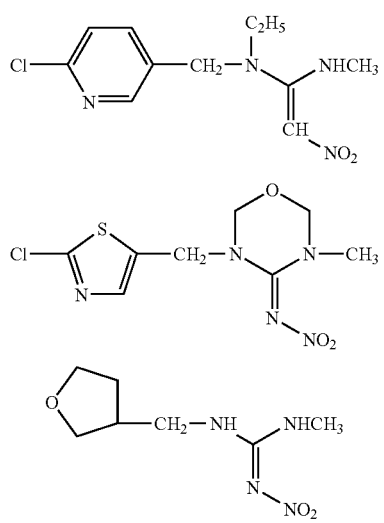

Furthermore, particular preference is given to the compounds

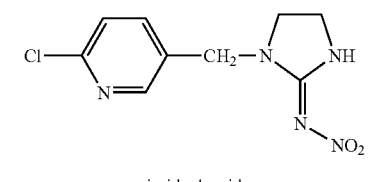
imidacloprid

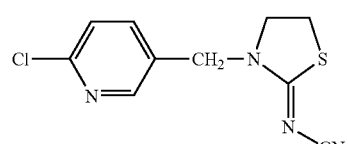
thiacloprid

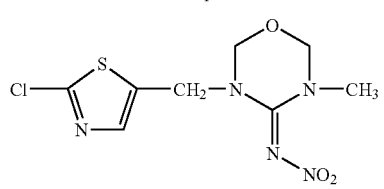
thiamethoxam

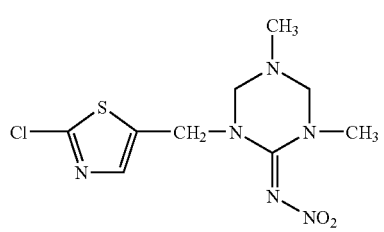

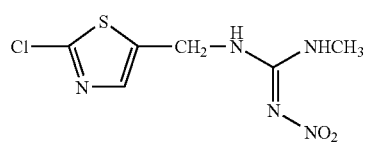

Carbamates which may be mentioned are substituted phenyl carbamates and naphthyl carbamates.

Phenylpyrazoles which may be mentioned are, for example, the following compounds:

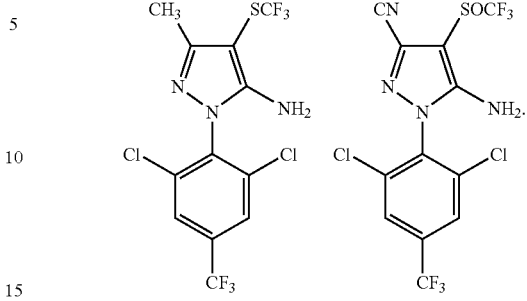

The following compounds may be mentioned as being preferred:

2-Oxobutylphenyl N-methylcarbamate,
4-Dimethylamino-3-methyl-phenyl N-methylcarbamate,
2-Isopropoxy-phenyl N-methylcarbamate,
1-Naphthyl N-methylcarbamate,
m-Tolyl N-methylcarbamate,
3,4-Xylyl N-methylcarbamate,
3,5-Xylyl N-methylcarbamate,
2-[1,3-Dioxolan-2-yl]phenyl N-methylcarbamate.

Phosphoric esters which may be mentioned as being preferred are the compounds with the common names phoxim, fenitrothion, dichlorvos, trichlorfon and malathion.

Juvenile hormones and juvenile-hormone-like substances, such as:

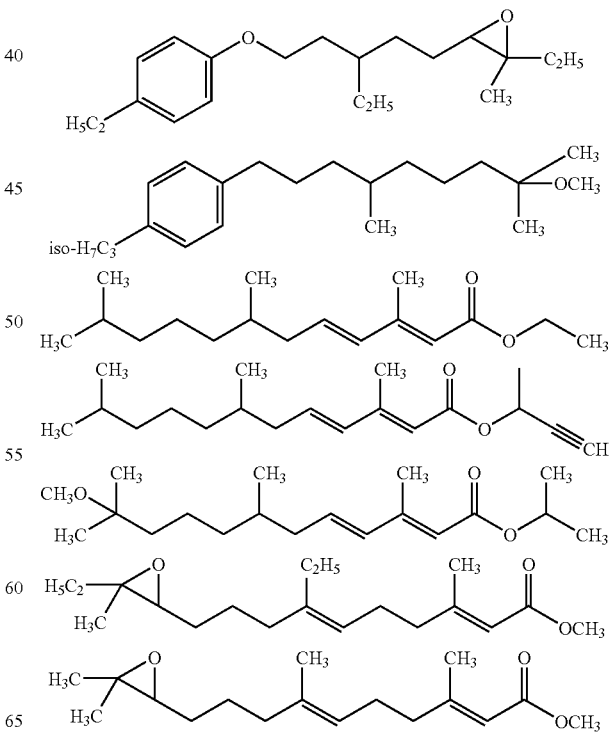

Substituted diaryl ethers, such as:

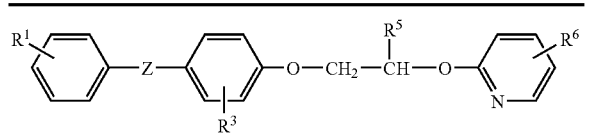

| R¹ | R³ | R⁵ | R⁶ | Z |
|---|---|---|---|---|
| H | H | CH₃ | 2-Cl | O |
| 5-F | H | CH₃ | H | O |
| H | H | CF₃ | H | O |
| H | H | C₂H₅ | H | O |
| H | H | H | H | O |
| H | H | CH₃ | H | CH₂ |
| H | H | CH₃ | H | C(CH₃)₂ |

Benzoylureas, such as:

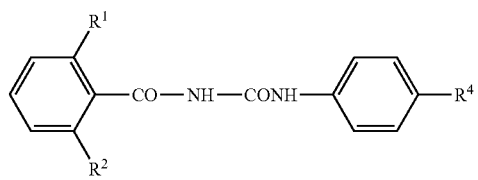

| R¹ | R² | R⁴ |
|---|---|---|
| H | Cl | CF₃ |
| Cl | Cl | CF₃ |
| F | F | CF₃ |
| H | F | CF₃ |
| H | Cl | SCF₃ |
| F | F | SCF₃ |
| H | F | SCF₃ |
| H | Cl | OCF₃ |
| F | F | OCF₃ |
| H | F | OCF₃ |
| F | F | O-C₆H₄-Cl (4-Cl) |
| F | F | O-C₆H₄-CF₃ (4-CF₃) |
| F | F | O-C₆H₄-CF₃ (4-CF₃) |

Triazines, such as:

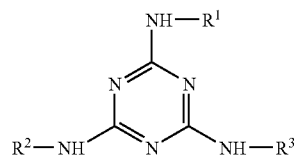

| R¹ | R² | R³ |
|---|---|---|
| cyclopropyl | H | H |
| cyclopropyl | H | CH₃ |
| cyclopropyl | H | C₂H₅ |

-continued

| R¹ | R² | R³ |
|---|---|---|
| cyclopropyl | H | C₃H₇-n |
| cyclopropyl | H | C₄H₉-n |
| cyclopropyl | H | C₅H₁₁-n |
| cyclopropyl | H | C₆H₁₃-n |
| cyclopropyl | H | C₇H₁₅-n |
| cyclopropyl | H | C₈H₁₇-n |
| cyclopropyl | H | C₁₂—H₂₅-n |
| cyclopropyl | H | CH₂—C₄H₉-n |
| cyclopropyl | H | CH₂CH(CH₃)C₂H₅ |
| cyclopropyl | H | CH₂CH=CH₂ |
| cyclopropyl | Cl | C₂H₅ |
| cyclopropyl | Cl | C₆H₁₃-n |
| cyclopropyl | Cl | C₈H₁₇-n |
| cyclopropyl | Cl | C₁₂H₂₅-n |
| cyclopropyl | H | cyclopropyl |
| cyclopropyl | H | COCH₃ |
| cyclopropyl | H | COCH₃ HCl |
| cyclopropyl | H | COC₂H₅ HCl |
| cyclopropyl | H | COC₂H₅ |
| cyclopropyl | H | COC₃H₇-n |
| cyclopropyl | H | COC₃H₇-i |
| cyclopropyl | H | COC₄H₉-t HCl |
| cyclopropyl | H | COC₄H₉-n |
| cyclopropyl | H | COC₆H₁₃-n |
| cyclopropyl | H | COC₁₁—H₂₃-n |
| cyclopropyl | COCH₃ | COC₂H₅ |
| cyclopropyl | COC₃H₇-n | COC₆H₁₃-n |
| cyclopropyl | COCH₃ | COC₃H₇-n |
| cyclopropyl | COC₂H₅ | COC₃H₇-n |
| cyclopropyl | H | COCyclopropyl |
| cyclopropyl | COCyclopropyl | COCyclopropyl |
| cyclopropyl | COCH₃ | COCH₃ |
| isopropyl | H | H |
| isopropyl | H | COCH₃ |
| isopropyl | H | COC₃H₇-n |
| cyclopropyl | H | CONHCH₃ |
| cyclopropyl | H | CONHC₃H₇-i |
| cyclopropyl | CONHCH₃ | CONHCH₃ |
| cyclopropyl | H | SCNHCH₃ |
| cyclopropyl | H | CONHCH₂CH=CH₂ |
| cyclopropyl | CONHCH₂CH=CH₂ | CONHCH₂CH=CH₂ |
| cyclopropyl | CSNHCH₃ | CSNHCH₃ |

The amounts of the combination compounds can be varied within wide limits between 0.1 and 12.5%, where particular preference is given to amounts in the range from 0.1 to 10.0% and very particular preference to the amounts in the range from 0.5 to 7.5%. Here, percentages are to be understood as percent by weight.

Particular preference is given to combinations of the pyrethroids and pyrethrins, in particular flumethrin, with chloronicotinyl compounds, in particular imidacloprid, thiamethoxam, chlothianidin, nitenpyram, acetamiprid and thiacloprid.

Preferred synergists for these compounds are piperonyl butoxide and sesame oil. These synergists are described, for ex ample, in the patent EP-413 610.

The chosen formulation auxiliaries based on polydimethysiloxanes having cationic quaternary amine groups of the formula

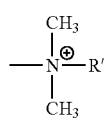

R' = various organic radicals are known polymeric or oligomeric compounds. By way of example, but not by way of limitation, the polysiloxanes described in EP-A 0017 121, p. 2, 1.11 to p. 3, 1.3, EP-A 0 017 122, p. 2, 1.11 to p. 3, 1.13, EP-A 0 166 122, p. 4, 1.31 to p. 7 in its entirety, EP-A 0 294 642, p. 5, 1.10 to p. 8, 1.51, EP-A 282 720, p. 6, 1.10 to p. 14, 1.54 and also those described in EP-A 0 164 668 on p. 4, 1.31 to p. 8, 1.3 may be mentioned.

To prepare the compositions according to the invention, it is possible to use polysiloxanes both with mono- and with polyquaterary amine groups. Of course, said polydimethylsiloxanes may have further functional groups, such as carboxylic acid, amine, hydroxyl, carboxylic ester. Very particularly preferred functional groups are hydroxyl and carboxylic acids. Their viscosity can be varied within wide limits in the range from 200 to 17,500 $mm^2s^{-1}$ (at 25° C.), measured in accordance with DIN 53 019 as a 50% strength aqueous solution, where particular preference is given to those having a viscosity in the range from 250 to 10,000 $mm^2s^{-1}$ (at 25° C.) and very particular preference is given to those having a viscosity in the range from 250 to 1350 $mm^2s^{-1}$ (at 25° C.).

Very particular preference is given to polysiloxanes of the Formula (V)

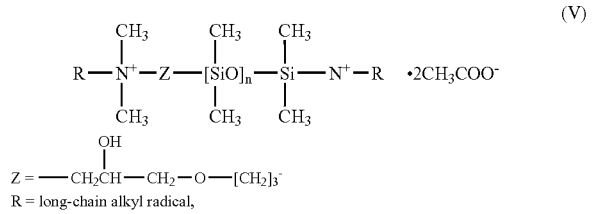

which are sold under the trade name ABIL® by Goldschmidt.

The amounts of polydimethylsiloxane used can be varied within wide limits between 0.1 and 15%, and preference is given to amounts in the range from 0.1 to 7.5%. To prepare the novel formulations according to the invention, particular preference is given to using amounts in the range from 0.25–2.5%. Here, the percentages are to be understood as meaning percent by weight.

Solvents used according to the invention are aliphatic polyethers, such as diethylene glycol monomethyl ether, dipropylene glycol monopropyl ether, cyclic carbonates, such as propylene carbonate, ethylene carbonate, aliphatic and aromatic alcohols, such as ethanol, isopropanol, acetates, such as benzyl acetate, benzyl benzoate, or mixtures thereof.

Particularly preferred solvents are diethylene glycol monomethyl ether, dipropylene glycol monopropyl ether, propylene carbonate, ethanol and isopropanol. For preparing the novel liquid formulations, very particular preference is given to using diethylene glycol monomethyl ether, dipropylene glycol monopropyl ether, ethanol and isopropanol and mixtures thereof.

In the formulation ac cording to the invention, the organic solvent fraction is from 2.5 to 99.8% by weight, preferably from 75 to 99.0% by weight and very particularly preferably from 80 to 92.5% by weight.

The proportion of water in the novel formulations can be varied within wide limits from 095% by weight, where particular preference is given to 0–15% by weight, and very particular preference to 5–17.5% by weight.

In addition, the formulations according to the invention may comprise customary auxiliaries, such as antioxidants or odour-masking agents.

Stabilizers and antioxidants which may be mentioned are sulphites or metabisulphites, such as potassium metabisulphite; organic acids, such as citric acid, ascorbic acid; phenols, butylhydroxytoluene, butylhydroxyanisole, tocopherol, where preference is given to the organic acids citric acid and malic acid. Very particularly preferred stabilizers are citric acid and butyhydroxytoluene. Their proportion may be varied within wide limits in the range from 0.05 to 2.5% by weight, and particular preference is given to amounts in the range from 0.075 to 0.15% by weight.

Odour-masking agents are, for example, mixtures of organic fatty esters. In the formulations according to the invention, they are preferably present in amounts of from 0.1 to 2% by weight.

Surprisingly, the liquid formulations according to the invention have an excellent storage stability of several years in all climate zones and are compatible with skin, user and environment. Surprisingly, they are also highly suitable for filling into, and offering for sale in, storage-critical "single dose polypropylene plastic tubes" with a wall thickness of 300–500 μm and a filling volume of from 1.0 to 4.0 ml.

Accordingly, such single-dose polypropylene plastic tubes filled with the compositions according to the invention also form part of the subject-matter of the present invention.

Moreover, the liquid formulations according to the invention have an unexpected synergistic, i.e. activity-enhancing effect, for example when the active compounds used are pyrethroids/pyrethrins.

The compositions according to the invention are environmentally compatible and, owing to the very low toxicity, user-friendly.

While being of low toxicity to warm-blooded species, the compositions according to the invention are suitable for the control of parasitic insects which are encountered in animal keeping and animal breeding in domestic and productive animals and in zoo and laboratory animals and animals used for experimentation and in the pursuit of hobbies. In this context they are active against all or individual stages of development of the pests and against resistant and normally sensitive species of the pests.

The pests include:

from the order of the *Anoplura* e.g. *Haematopinus* spp., *Linognathus* spp., *Solenopotes* spp., *Pediculus* spp., *Pthirus* spp.;

from the order of the *Mallophaga* e.g. *Trimenopon* spp., *Menopon* spp., *Eomenacanthus* spp., *Menacanthus* spp., *Trichodectes* spp., *Felicola* spp., *Damalinea* spp., *Bovicola* spp;

from the order of the *Diptera* e.g. *Chrysops* spp., *Tabanus* spp., *Musca* spp., *Hydrotaea* spp., *Muscina* spp., *Haematobosca* spp., *Haematobia* spp., *Stomoxys* spp., *Fannia* spp., *Glossina* spp., *Lucilia* spp., *Calliphora* spp., *Auchmeromyia* spp., *Cordylobia* spp., *Cochliomyia* spp., *Chrysomyia* spp., *Sarcophaga* spp., *Wohlfartia* spp., *Gasterophilus* spp., *Oesteromyia* spp., *Oedemagena* spp., *Hypoderma* spp., *Oestrus* spp., *Rhinoestrus* spp., *Melophagus* spp., *Hippobosca* spp.;

from the order of the *Siphonaptera* e.g. *Ctenocephalides* spp., *Echidnophaga* spp., *Ceratophyllus* spp.

Particular mention may be made of the action against *Siphonaptera*, especially against fleas and ticks.

The productive and breeding animals include mammals such as, for example, cattle, horses, sheep, pigs, goats, camels, water buffalo, donkeys, rabbits, fallow deer, reindeer, fur-bearing animals such as, for example, mink, chinchilla or racoon, birds such as, for example, chickens, geese, turkeys, ducks.

Laboratory animals and those for experimentation include mice, rats, guinea pigs, golden hamsters, dogs and cats.

The animals used in the pursuit of hobbies include dogs and cats.

Particular emphasis is given to the use in cats and dogs.

Application can be both prophylactically and therapeutically.

To prepare the formulation according to the invention, appropriate amounts of the desired components are mixed with one another, for example by using conventional stirred tanks or other suitable apparatus.

If required for the ingredients, it is also possible to operate under a protective atmosphere or other methods of excluding oxygen.

The examples below serve to illustrate the invention:

EXAMPLE 1

A homogeneous pump-spray formulation (100 ml) comprising

| | |
|---|---|
| 0.30 g | of flumethrin |
| 27.05 g | of diethylene glycol monoethyl ether |
| 50.50 g | of isopropanol |
| 7.50 g | of water |
| 1.00 g | of Abil Quat 3272 (1) |
| 0.1 g | of citric acid |
| 0.6 g | of Marena PH 99000 |

(1) Abil Quat 3272, 50% strength, is a 50% strength aqueous polydimethyl-siloxane solution featuring a diquaternary ammonium group and a viscosity range of 1000 +/− 200 [$mm^2.s-1$] at 25° C. from Goldschmidt AG D-4300 Essen In a placebo-controlled laboratory experiment (PLRS 9806) to test the activity of the formulation mentioned under Example 1, a total of 20 dogs (different breeds, male and female) were used. All animals were infested twice, on days −5 and −1 before the treatment, in each case with 60 ticks (*Rhipicephalus sanguineus, Dermacentor variabilis*). On the day of the treatment, the parasitic ticks on the dogs were counted, and the dogs were ranked according to the number of parasites. Alternating, all animals were assigned to one of the two test groups. The animals of Test group 1 were given about 3 ml of the formulation mentioned under Example 1 per kilogram of body weight. The animals of Test group 2 were treated with about 3 ml of a placebo formulation per kilogram of body weight. In both groups, application was carried out by spraying the entire surface of the body.

Examination for action on ticks which were already parasitizing was carried out by once more counting, on the two following days, the ticks on each dog. It was found that the activity of the formulation mentioned under Example 1 was 96.3% on the second day after treatment, compared to the placebo formulation.

Examination for long-term activity (protection against reinfestation) was carried out by weekly reinfestation with in each case 60 ticks per animal. It was possible to demonstrate that, in both test groups, for at least 5 weeks, none or only a few individual ticks start sucking. Furthermore, the formulations were tolerated well.

EXAMPLE 2

A homogeneous pump-spray formulation (100 ml) comprising

| | |
|---|---|
| 0.30 g | of flumethrin |
| 27.65 g | of diethylene glycol monoethyl ether |
| 50.50 g | of isopropanol |
| 7.50 g | of water |
| 1.00 g | of Abil Quat 3274 (2) |
| 0.1 g | of citric acid |

(2) Abil Quat 3274 is a 50% strength aqueous polydimethylsiloxane solution featuring a diquaternary ammonium group and a viscosity range of 5000–15,000 [$mm^2.s-1$] at 25° C. from Goldschmidt AG D-4300 Essen In an controlled laboratory experiment (GZ 49/97) to test the activity of the formulation mentioned under Example 2, a total of 10 dogs (Retrievers, Labradors, Setters, male and female) were used. All animals were infested once, on day −3 before the treatment, with in each case 70 ticks (*Rhipicephalus sanguineus, Ixodes canisuga*). On the day of the treatment, the parasitizing ticks on the dogs were counted, and the dogs were ranked according to the number of parasites. Alternatingly, all animals were assigned to one of the two test groups. The animals of Test group 1 were given about 3 ml of the formulation mentioned under Example 2 per kilogram of body weight. The animals of Test group 2 remained untreated. In Test group 1, application was carried out by spraying the entire surface of the body.

Examination for action on ticks which were already parasitizing was carried out by once more counting, on the two following days, the ticks on each dog. It was found that the activity of the formulation mentioned under Example 2 was 100% on the third day after treatment, compared to the untreated control group.

Examination for long-term activity (protection against reinfestation) was carried out by weekly reinfestation with in each case 0.70 ticks per animal. It was possible to demonstrate that, in both test groups, for 5 to 7 weeks, none or only a few individual ticks started sucking. Furthermore, the formulations were tolerated well.

EXAMPLE 3

A homogeneous pump-spray formulation (100 ml) comprising

| | |
|---|---|
| 0.30 g | of flumethrin |
| 27.05 g | of dipropylene glycol monomethyl ether |
| 50.50 g | of ethanol |
| 7.50 g | of water |
| 1.00 g | of Abil Quat 3272 (1) |
| 0.1 g | of citric acid |
| 0.6 g | of Marena PH 99000 |

The laboratory tests on activity against ticks according to Example 2 show that the formulation is highly active against ticks.

EXAMPLE 4

A homogeneous pump-spray formulation (100 ml) comprising

| | |
|---|---|
| 0.30 g | of flumethrin |
| 27.35 g | of diethylene glycol monoethyl ether |
| 50.50 g | of isopropanol |
| 7.50 g | of water |
| 1.00 g | of Abil Quat 3272 (1) |
| 0.1 g | of citric acid |
| 0.3 g | of imidacloprid |

The laboratory tests on activity against ticks according to Example 2 show that the formulation is highly active against ticks and very suitable for controlling ticks.

To determine the activity against fleas of the formulation, a total of 10 dogs (Retrievers, Labradors, Setters, male and female) were used. All animals were infected once, on day −3 before the treatment, in each case with 100 fleas. On the day of the treatment, the parasitic fleas on the dogs were counted and the dogs were ranked according to the number of parasites. Alternatingly, all animals were assigned to one of the test groups. The animals of Test group 1 were given about 3 ml of the formulation mentioned under Example 2 per kilogram of body weight. The animals of Test group 2 remained untreated. In Test group 1, application was carried out by spraying the entire surface of the body.

Examination for action on fleas which were already parasitizing was carried out by once more counting, on the following days, the fleas on each dog. It was found that the activity of the formulation mentioned under Example 4 was 100% on the second day after treatment, compared to the untreated control group. On day 7, 14, 21 and 28 after the treatment, the animals were then infected with in each case 100 fleas. In each case on day 8, 15, 22 and 29 after the treatment, the fleas which remained on the dog were counted. No living fleas were found. The activity against fleas was 100%.

EXAMPLE 5

A homogenous pump-spray formulation (100 ml) comprising

| | |
|---|---|
| 0.30 g | of flumethrin |
| 27.35 g | of diethylene glycol monoethyl ether |
| 50.50 g | of isopropanol |
| 7.50 g | of water |
| 1.00 g | of Abil Quat 3272 (1) |
| 0.1 g | of citric acid |
| 0.3 g | of pyriproxyfen |

The laboratory tests on activity against ticks according to Example 2 show that the formulation is highly active against ticks and very suitable for controlling ticks. Furthermore, it was possible to demonstrate that the formulation is highly suitable for controlling flea larvae. For up to 45 days after the treatment, the action against flea larvae was 100%.

EXAMPLE 6

A homogeneous spot-on formulation (100 ml) comprising

| | |
|---|---|
| 2.00 g | of flumethrin |
| 81.00 g | of diethylene glycol monoethyl ether |
| 15.00 g | of water |
| 2.00 g | of Abil Quat 3272 (1) |
| 0.1 g | of citric acid |
| 0.1 g | of BHT (butylhydroxytoluene) |

EXAMPLE 7

A homogeneous spot-on formulation (100 ml) comprising

| | |
|---|---|
| 2.00 g | of flumethrin |
| 76.00 g | of diethylene glycol monoethyl ether |
| 15.00 g | of water |
| 2.00 g | of Abil Quat 3272 (1) |
| 5.00 g | of piperonyl butoxide |
| 0.1 g | of citric acid |
| 0.1 g | of BHT (butylhydroxytoluene) |

In a laboratory experiment without control (GZ 35/99) to test the activity of the formulations mentioned under Examples 6 and 7, a total of 15 dogs (Beagle, male and female) were used. All animals were infested once, on day −2 before the treatment, in each case with 50 ticks (Rhipicephalus sanguineus). On the day of the treatment, the parasitizing ticks on the dogs were counted, and the dogs were ranked according to the number of parasites. Alternatingly, all animals were assigned to one of the two test groups. The animals of Test group 1 were given 0.4 ml of the formulation mentioned under Example 7 per kilogram of body weight. The animals of Test group 2 were treated with 0.4 ml of the formulation mentioned under Example 6 per kilogram of body weight. In both groups, application was carried out directly on to the skin in the area of the neck and the area of the back, where the total dose applied was in each case 1 ml/skin area (spot).

Examination for activity on ticks which were already parasitizing was carried out by once more counting, on the two following days, the ticks on each dog. It was found that, on the second day after the treatment, 64% of all sucking ticks had been killed by the formulation mentioned under Example 7. When the formulation mentioned under Example 6 was used, the corresponding number was 73%.

Examination for long-term activity (protection against reinfestation) was carried out by weekly reinfestation with in each case 50 ticks per animal. It was possible to demonstrate that, in both test groups, for at least 6 weeks none or only a few individual ticks start sucking. Furthermore, placebo- and active-compound containing formulations were tolerated well.

EXAMPLE 8

An aqueous homogeneous emulsion spot-on formulation (100 ml) comprising

| | |
|---|---|
| 2.00 g | of flumethrin |
| 4.00 g | of diethylene glycol monoethyl ether |

-continued

| | |
|---|---|
| 63.45 g | of water |
| 10.00 g | of Abil Quat 3272 (1) |
| 30.00 g | of urea |
| 0.1 g | of citric acid |

The laboratory tests on activity against ticks according to Examples 6 and 7 show that the formulation has good activity against ticks and is very suitable for controlling ticks.

EXAMPLE 9

A homogeneous spot-on formulation (100 ml) comprising

| | |
|---|---|
| 1.00 g | of flumethrin |
| 5.00 g | of piperonyl butoxide |
| 2.50 g | of imidacloprid |
| 15.00 g | of water |
| 2.00 g | of Abil Quat 3272 (1) |
| 74.77 g | of diethylene glycol monoethyl ether |
| 0.13 g | of citric acid |
| 0.10 g | of BHT (butylhydroxytoluene) | was used for carrying out activity studies on dogs against ticks and against fleas according to Example 4. The application volume was 0.4 ml/kg of body weight. Action of the formulation against fleas and ticks was 100%, combined with a long-term action of at least 5 weeks.

The analytical stress studies show that the formulation according to the invention is highly suitable for filling into single-dose PP tubes with a total filling volume of <10 ml and a wall thickness of ~350 μm and has a long-term stability of at least 36 months in all climate zones.

EXAMPLE 10

A homogeneous spot-on formulation (100 ml) comprising

| | |
|---|---|
| 1.00 g | of flumethrin |
| 5.00 g | of piperonyl butoxide |
| 2.50 g | of chlothianidine |
| 15.00 g | of water |
| 2.00 g | of Abil Quat 3272 (1) |
| 74.77 g | of diethylene glycol monoethyl ether |
| 0.13 g | of citric acid |
| 0.10 g | of BHT (butylhydroxytoluene) | was used for carrying out activity studies on dogs against ticks and against fleas according to Example 4. The application volume was 0.4 ml/kg of body weight. Action of the formulation against fleas and ticks was 100%, combined with a long-term action of at least 5 weeks. The novel formulation has excellent skin compatibility.

The analytical stress studies show that the formulation according to the invention is highly suitable for filling into single-dose PP tubes with a total filling volume of <10 ml and a wall thickness of ~350 μm and has a long-term stability of at least 36 months in all climate zones.

EXAMPLE 11

A homogeneous spot-on formulation (100 ml) comprising

| | |
|---|---|
| 1.00 g | of flumethrin |
| 5.00 g | of piperonyl butoxide |
| 2.50 g | of thiamethoxam |
| 15.00 g | of water |
| 2.00 g | of Abil Quat 3272 (1) |
| 74.77 g | of diethylene glycol monoethyl ether |
| 0.13 g | of citric acid |
| 0.10 g | of BHT (butylhydroxytoluene) |
| 0.10 g | of tocopherol (Vitamin E) | was used for carrying out activity studies on dogs against ticks and against fleas according to Example 4. The application volume was 0.4 ml/kg of body weight. Action of the formulation against fleas and ticks was 100%, combined with a long-term action of at least 4 weeks.

The analytical stress studies show that the formulation according to the invention is highly suitable for filling into single-dose PP tubes with a total filling volume of <10 ml and a wall thickness of ~350 μm and has a long-term stability of at least 36 months in all climate zones. The novel formulation according to the invention is skin-compatible and irritation-free.

EXAMPLE 12

A homogeneous spot-on formulation (100 ml) comprising

| | |
|---|---|
| 1.00 g | of flumethrin |
| 5.00 g | of piperonyl butoxide |
| 3.50 g | of thiacloprid |
| 15.00 g | of water |
| 2.00 g | of Abil Quat 3272 (1) |
| 73.77 g | of diethylene glycol monoethyl ether |
| 0.13 g | of citric acid |
| 0.10 g | of BHT (butylhydroxytoluene) | was used for carrying out activity studies on dogs against ticks and against fleas according to Example 4. The application volume was 0.30 ml/kg of body weight. Action of the formulation against fleas and ticks was 100%, combined with a long-term action of at least 4 weeks.

The analytical stress studies show that the formulation according to the invention is highly suitable for filling into single-dose PP tubes with a total filling volume of <10 ml and a wall thickness of ~350 μm and has a long-term stability of at least 36 months in all climate zones. The compatibility studies show that the novel formulation does not cause any skin irritations.

EXAMPLE 13

A homogeneous spot-on formulation (100 ml) comprising

| | |
|---|---|
| 2.00 g | of flumethrin |
| 5.00 g | of piperonyl butoxide |
| 4.50 g | of acetamiprid |
| 15.00 g | of water |
| 2.00 g | of Abil Quat 3272 (1) |
| 71.77 g | of diethylene glycol monoethyl ether |
| 0.13 g | of citric acid |
| 0.10 g | of BHT (butylhydroxytoluene) | was used for carrying out activity studies on dogs against ticks and against fleas according to Example 4. The application volume was 0.35 ml/kg of body weight. Action of the formulation against fleas and ticks was 100%, combined with a long-term action of at least 4 weeks.

The analytical stress studies show that the formulation according to the invention is highly suitable for filling into single-dose PP tubes with a total filling volume of <10 ml and a wall thickness of ~350 µm and has a long-term stability of at least 36 months in all climate zones. The novel formulation has excellent skin compatibility.

EXAMPLE 14

A homogeneous spot-on formulation (100 ml) comprising

| | |
|---|---|
| 2.00 g | of flumethrin |
| 5.00 g | of piperonyl butoxide |
| 15.00 g | of nitenpyram |
| 2.00 g | of Abil Quat 3272 (1) |
| 71.77 g | of diethylene glycol monoethyl ether |
| 0.13 g | of citric acid |
| 0.10 g | of BHT (butylhydroxytoluene) | was used for carrying out activity studies on dogs against ticks and against fleas according to Example 4. The application volume was 0.30 ml/kg of body weight. Action of the formulation against fleas and ticks was 100%, combined with a long-term action of at least 4 weeks.

The analytical stress studies show that the formulation according to the invention is highly suitable for filling into single-dose pp tubes with a total filling volume of <10 ml and a wall thickness of ~350 µm and has a long-term stability of at least 36 months in all climate zones.

What is claimed is:

1. A composition comprising (a) at least one active ingredient for topical control of parasitic insects on animals, wherein said active ingredient comprises an effective amount of flumethrin, and (b) at least one polysiloxane comprising at least one quaternary ammonium group in an amount sufficient to provide low amounts of dermal irritation for said animal.

2. The composition of claim 1, further comprising imidacloprid.

3. A single dose polypropylene tube having a wall thickness of about 350 µm and a total filling volume of less than about 10 µm, wherein said tube is filled with the composition of claim 1.

* * * * *